(12) United States Patent
Che et al.

(10) Patent No.: US 6,290,653 B1
(45) Date of Patent: Sep. 18, 2001

(54) BLOOD PRESSURE CUFF FOR SPHYGMOMANOMETER

(75) Inventors: Tae Young Che, Seoul; Jong In Jeung, Anyang; Won Sub Son, Taejon, all of (KR)

(73) Assignee: Sein Electronics Co., Ltd. (KR)

( * ) Notice: Subject to any disclaimer, the term of this patent is extended or adjusted under 35 U.S.C. 154(b) by 0 days.

(21) Appl. No.: 09/412,715

(22) Filed: Oct. 5, 1999

(30) Foreign Application Priority Data

Jun. 30, 1999 (KR) .................................................. 99-12675

(51) Int. Cl.$^7$ ....................................................... A61B 5/02

(52) U.S. Cl. ........................................... 600/490; 600/499

(58) Field of Search ........................... 600/485, 490–499, 600/500; 606/202–203

(56) References Cited

U.S. PATENT DOCUMENTS 4,354,503 * 10/1982 Golden .................................. 600/499
5,413,582 * 5/1995 Eaton ................................ 600/499 X

* cited by examiner

Primary Examiner—Eric F. Winakur
Assistant Examiner—Ryan Carter
(74) Attorney, Agent, or Firm—Galgano & Burke

(57) ABSTRACT

Disclosed is a blood pressure cuff for a sphygmomanometer, adapted for attachment to the upper arm of a user to effect blood pressure measurement for the user. The blood pressure cuff comprises an air bag disposed in the blood pressure cuff which has both ends coupled with each other to define a closed loop; an attachment tab extending from a side of the blood pressure cuff; a Velcro brand hook and loop fastener strip secured to a surface of the attachment tab; and a complementary Velcro brand hook and loop fastener strip secured to an outer surface of the blood pressure cuff such that it can be engaged with the Velcro brand hook and loop fastener strip.

2 Claims, 6 Drawing Sheets

BLOOD PRESSURE CUFF FOR SPHYGMOMANOMETER

BACKGROUND OF THE INVENTION

1. Field of the Invention

The present invention relates to a blood pressure cuff for a sphygmomanometer, and more particularly, the present invention relates to a blood pressure cuff which is adapted for being used in an independent-measurement type sphygmomanometer.

2. Description of the Related Art

The human body performs metabolism through blood, and therefore, it is necessary to frequently measure a blood pressure to confirm a condition of one's health. Generally, the term 'blood pressure' means an arterial blood pressure of the brachial artery.

The conventional blood pressure measuring method is typically implemented by wrapping a blood pressure cuff around the upper arm containing an artery, inflating the blood pressure cuff to a predetermined pressure thereby to occlude the artery, gradually reducing the pressure to allow increased blood flow through the artery, and measuring blood pressures at the times when the Korotkov sounds are generated and vanished as blood flow is restarted in the brachial artery thereby to determine a maximum blood pressure and a minimum blood pressure.

An electronic sphygmomanometer is a device in which an air bag is inflated with air supplied from an air pump to occlude the brachial artery and the air is deflated from the air bag to the outside to depressurize the air bag, and times when the Korotkov sounds are generated and vanished and blood pressures at that times are measured to render numerical expressions, thereby enabling blood pressure measurement to be conveniently carried out.

Referring to FIG. 1, there is shown a perspective view illustrating a construction and usage of a blood pressure cuff for a dependent-measurement type sphygmomanometer of the conventional art, which is most widely used. The blood pressure cuff 11 includes an air bag (not shown). The air bag is disposed in the blood pressure cuff 11 and is connected via an air hose 15 to a main body (not shown) of the sphygmomanometer. The blood pressure cuff 11 has a shape of an elongate rectangle. A Velcro brand hook and loop fastener strip 13 and a complementary Velcro brand hook and loop fastener strip 14 are secured to both ends of the blood pressure cuff 11, respectively, thereby enabling the blood pressure cuff 11 to be firmly attached to the upper arm U of the human body M.

The blood pressure cuff 11 constructed as mentioned above and shown in FIG. 1 can be used with no problem in the case that it is attached to the upper arm U of the human body M by a separate measurer M'.

However, recently, as an independent-measurement type sphygmomanometer is widely distributed as being an electronic sphygmomanometer, the blood pressure cuff 11 as shown in FIG. 1 suffers from defects in that it is difficult for a user to independently and personally attach the blood pressure cuff 11 to the upper arm U of one arm with the hand of the other arm.

To cope with this problem, for an independent-measurement type sphygmomanometer, a blood pressure cuff 21 as shown in FIG. 2 is used. A D-ring R is provided to one end of the blood pressure cuff 21, and an attachment tab 22 is formed at the other end of the blood pressure cuff 21. A Velcro brand hook and loop fastener strip 23 is secured to the attachment tab 22, and a complementary Velcro brand hook and loop fastener strip 21a is secured to an outer surface of the blood pressure cuff 21. In the blood pressure cuff 21 constructed as mentioned above, a user inserts his one hand H into a loop, as shown in FIG. 2A, which is defined by the fact that the attachment tab 22 is passed through the D-ring R, and then, the blood pressure cuff 21 is raised to the upper arm U using the other hand H'.

Thereafter, as shown in FIG. 2B, the attachment tab 22 is pulled by the other hand H' and is folded back to engage the Velcro brand hook and loop fastener strip 23 with the complementary Velcro brand hook and loop fastener strip 21a, thereby to complete the attachment of the blood pressure cuff 21 to the upper arm U.

Then, as shown in FIG. 2C, air is supplied via an air hose 24 into an air bag A disposed in the blood pressure cuff 21, from an air pump (not shown) of a main body of the independent-measurement type sphygmomanometer, thereby pressing the upper arm U to occlude the artery.

However, since a pressure of air supplied into the air bag A must have an extent to block blood flow in the brachial artery, it causes the human body M to experience compression which leads to pain. Also, because the D-ring R is made of metal having substantial rigidity, considerably large deformation stress is induced therein. As a result, the independent-measurement type sphygmomanometer is still encountered with a problem in that the D-ring R can be deformed or detached from the blood pressure cuff 21 and the blood pressure cuff 21 can cause pain or stress to the user thereby preventing an accurate blood pressure measurement from being obtained.

SUMMARY OF THE INVENTION

Accordingly, the present invention has been made in an effort to solve the problems occurring in the related art, and an object of the present invention is to provide a blood pressure cuff for a sphygmomanometer, which does not cause pain or stress to a user thereby not inducing an inaccurate blood pressure measurement and is not likely to be damaged thereby improving its durability.

In order to achieve the above object, according to one aspect of the present invention, there is provided a blood pressure cuff for a sphygmomanometer, adapted for attachment to the upper arm of a user to effect blood pressure measurement for the user, the blood pressure cuff comprising: an air bag disposed in the blood pressure cuff which has both ends coupled with each other to define a closed loop; an attachment tab extending from a side of the blood pressure cuff; a Velcro brand hook and loop fastener strip secured to a surface of the attachment tab; and a complementary Velcro brand hook and loop fastener strip secured to an outer surface of the blood pressure cuff such that it can be engaged with the Velcro brand hook and loop fastener strip.

By the features of the present invention, the blood pressure cuff can be attached to the upper arm of a user by the fact that the user fits the blood pressure cuff around the upper arm of himself, pulls the attachment tab and engages the Velcro brand hook and loop fastener strip with the complementary Velcro brand hook and loop fastener strip.

Therefore, the blood pressure cuff according to the present invention provides advantages in that since a D-ring made of metal is not used, possibility for the D-ring to be deformed or detached from the blood pressure cuff is eliminated in advance and irregularity of blood pressure due to pain or stress is not caused, whereby convenience and reliability in use and accuracy of a blood pressure measurement operation are ensured.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF PREFERRED EMBODIMENTS

Figure 1:
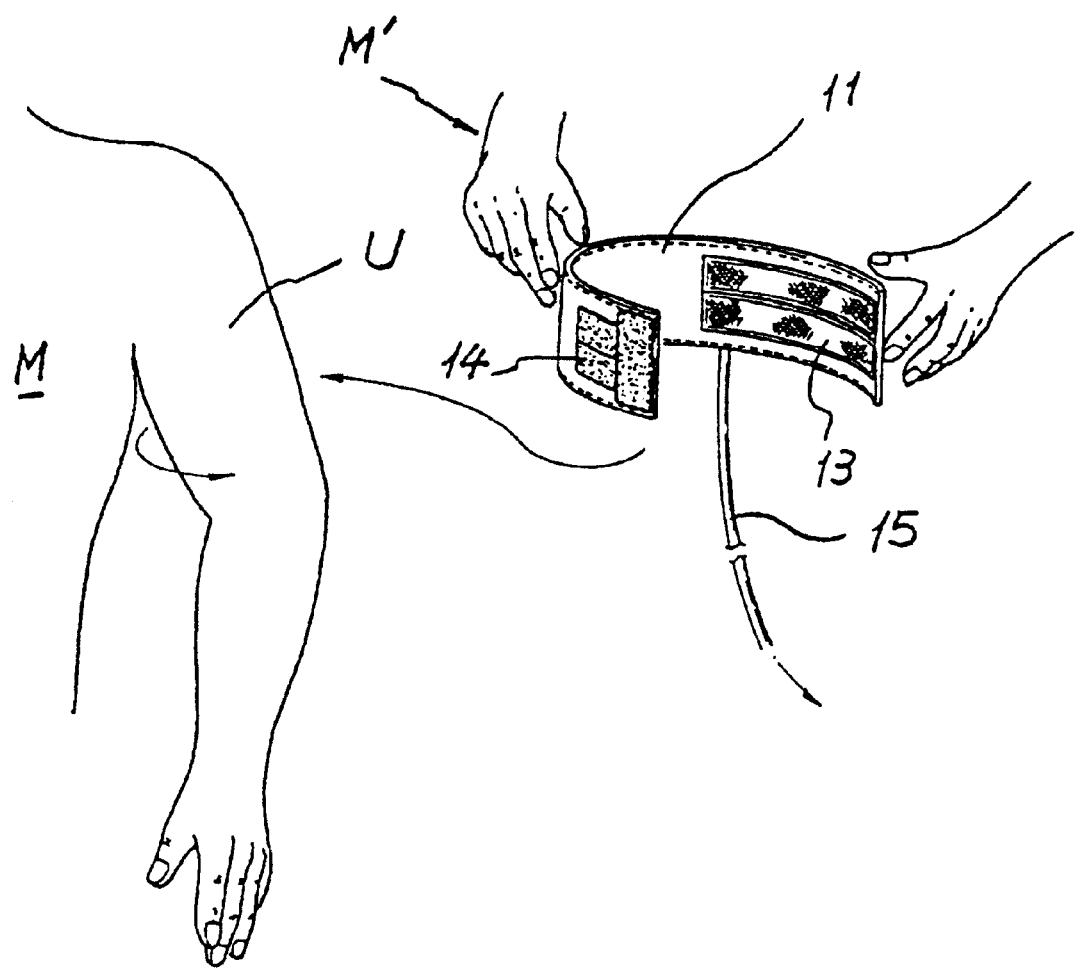
FIG. 1 is a perspective view illustrating a construction and usage of a blood pressure cuff for a dependent-measurement type sphygmomanometer of the conventional art.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 3A:
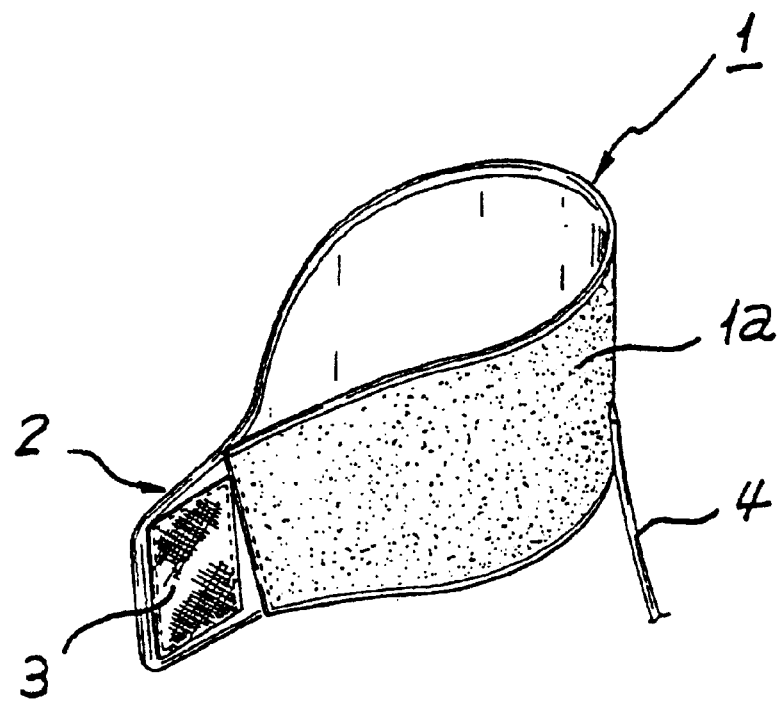
FIGS. 3A and 3B are respectively a perspective view and a side view illustrating a construction of a blood pressure cuff for a sphygmomanometer in accordance with an embodiment of the present invention.
Figure 3B:
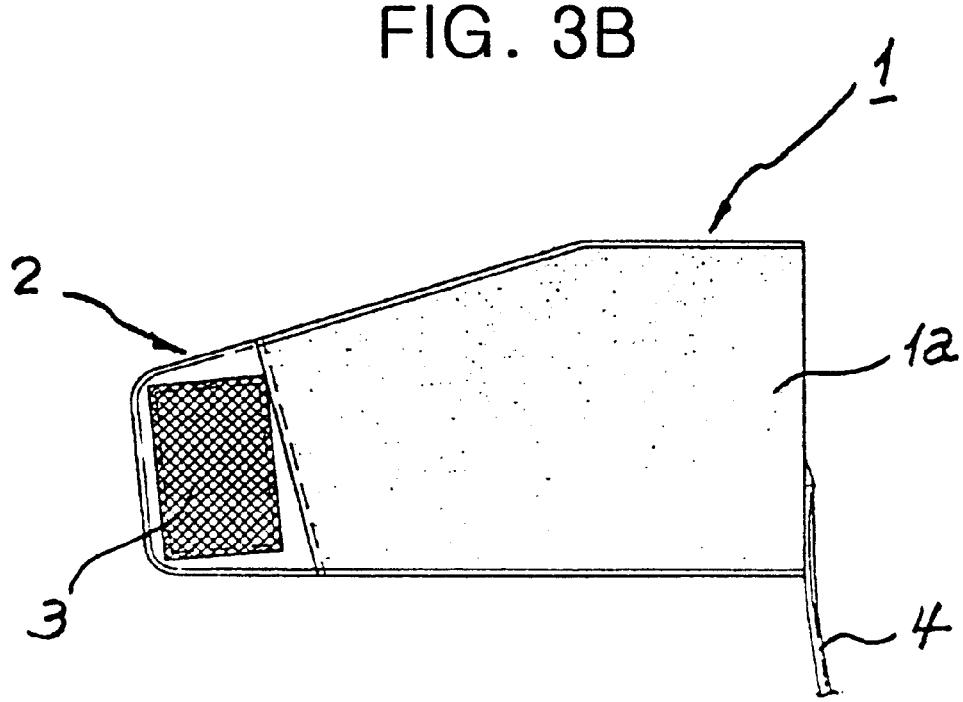

Referring to FIGS. 3A and 3B, a blood pressure cuff 1 having an air bag (not shown) disposed therein defines a closed loop due to the fact that both ends thereof are coupled with each other in accordance with characteristics of the present invention. An attachment tab 2 having a Velcro brand hook and loop fastener strip 3 secured thereto extends from a side of the blood pressure cuff 1. On the other hand, a complementary Velcro brand hook and loop fastener strip 1a is secured to an outer surface of the blood pressure cuff 1 which corresponds to the Velcro brand hook and loop fastener strip 3 of the attachment tab 2. The Velcro brand hook and loop fastener strip 3 can be engaged with the complementary Velcro brand hook and loop fastener strip 1a. The drawing reference numeral 4 represents an air hose which is connected to a body (not shown) of a sphygmomanometer.

In the shown embodiment, it is preferred that the attachment tab 2 is formed by an extension of one end of the blood pressure cuff 1. The other end of the blood pressure cuff 1 is coupled to a portion of the blood pressure cuff 1 adjacent to an end of the Velcro brand hook and loop fastener strip 3 which is positioned inside of the blood pressure cuff 1, by means of stitching, ultrasonic fusion, etc. to define the closed loop having substantially a shape of ρ.

In this case, it is also preferred that the blood pressure cuff 1 has a width which is gradually decreased in a direction toward the attachment tab 2, to improve the fit of the cuff about the user's arm. Moreover, because an upper part of the upper arm U has a thickness which is larger than that of a lower part of the upper arm U, while it is not essential in the present invention, it is preferred that the blood pressure cuff 1 is inclined downward and inward such that an upper portion of the blood pressure cuff 1 has an inner diameter which is larger than that of a lower portion of the blood pressure cuff 1, to ensure an adequate attachment of the blood pressure cuff 1 to the upper arm U.

FIGS. 4A through 4E are transverse cross-sectional views illustrating an attachment procedure of the blood pressure cuff 1 for a sphygmomanometer according to the present invention. In FIGS. 4A through 4E, the body M of a user and the upper arm U are depicted in an enlarged manner in view of clarity of illustration and explanation.

Figure 4A:
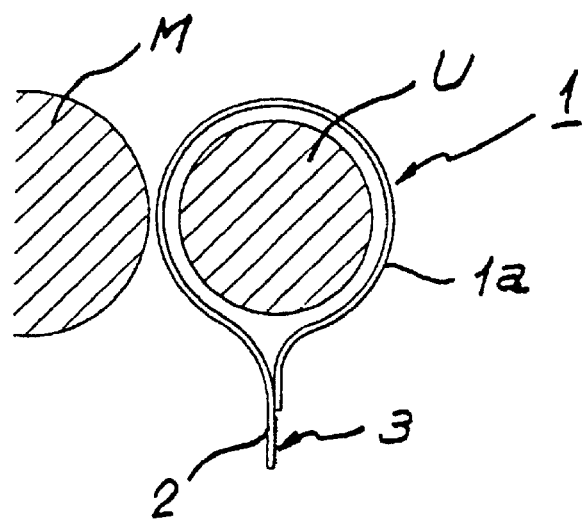
FIGS. 4A through 4E are transverse cross-sectional views illustrating usage of the blood pressure cuff for a sphygmomanometer according to the present invention.

Referring to FIG. 4A, the user inserts his one hand into the blood pressure cuff 1 defining the closed loop according to the present invention, and then, by raising the blood pressure cuff 1 toward the upper arm U using the other hand, the blood pressure cuff 1 is positioned around the upper arm U of the one arm.

Figure 4B:
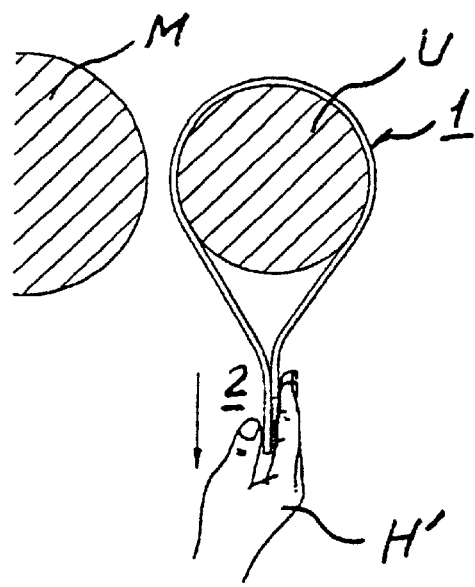
Figure 4C:
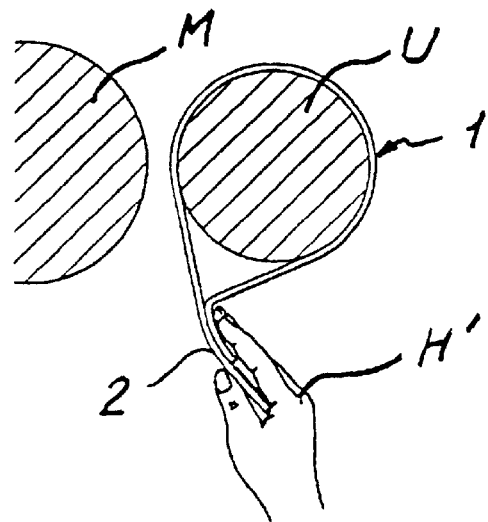

Then, after the attachment tab 2 is pulled using the other hand H' as shown in FIG. 4B, the blood pressure cuff 1 is folded at a portion where the middle finger of the user is positioned as shown in FIG. 4C such that the Velcro brand hook and loop fastener strip 3 of the attachment tab 2 is directed toward the complementary Velcro brand hook and loop fastener strip 1a.

Figure 4D:
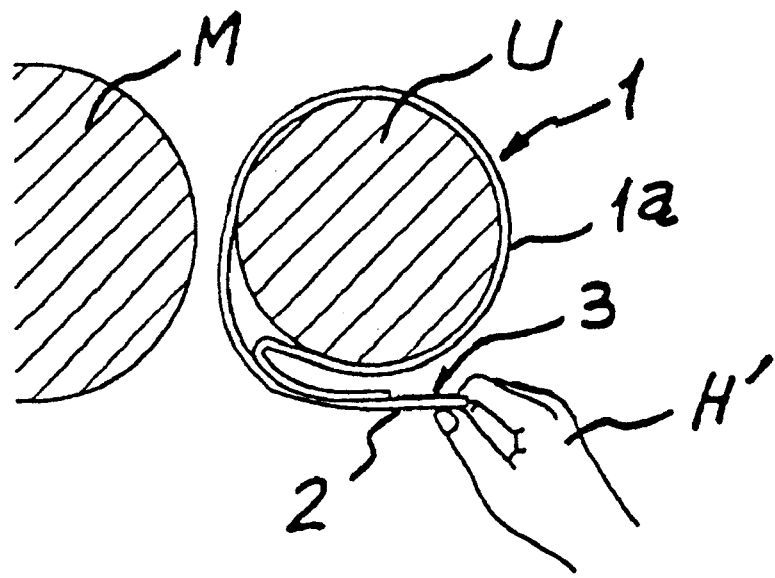
Figure 4E:
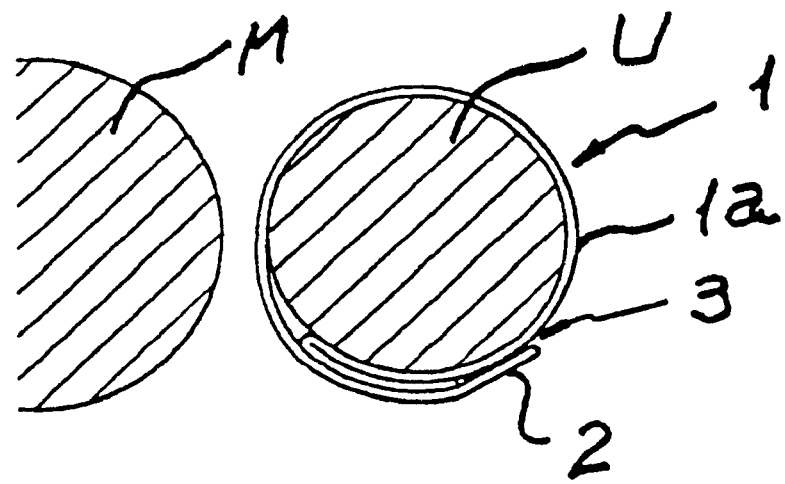

By continuously folding the blood pressure cuff 1 as shown in FIG. 4D while pulling the attachment tab 2, the blood pressure cuff 1 forms a U-shaped cross-section. Thereafter, by pressing the attachment tab 2 against the outer surface of the blood pressure cuff 1, the Velcro brand hook and loop fastener strip 3 of the attachment tab 2 is engaged with the complementary Velcro brand hook and loop fastener strip 1a, thereby to complete attachment of the blood pressure cuff 1 to the upper arm U.

According to this, it is possible to measure a blood pressure of the user's body M in accordance with the conventional method for using an electronic sphygmomanometer.

Figure 2A:
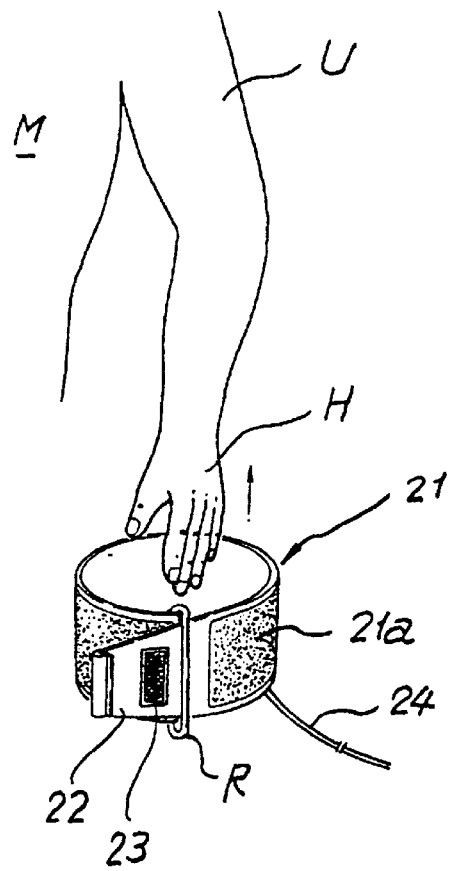
FIGS. 2A through 2C are perspective views and a partially cross-sectioned perspective view illustrating a construction and usage of a blood pressure cuff for an independent-measurement type sphygmomanometer of the conventional art.
Figure 2B:
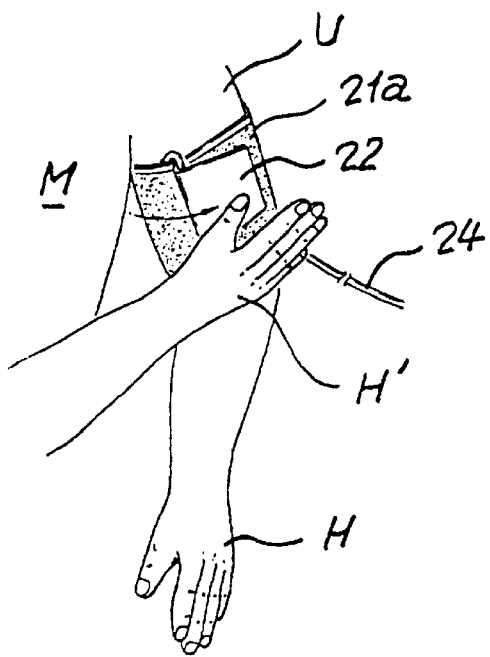
Figure 2C:
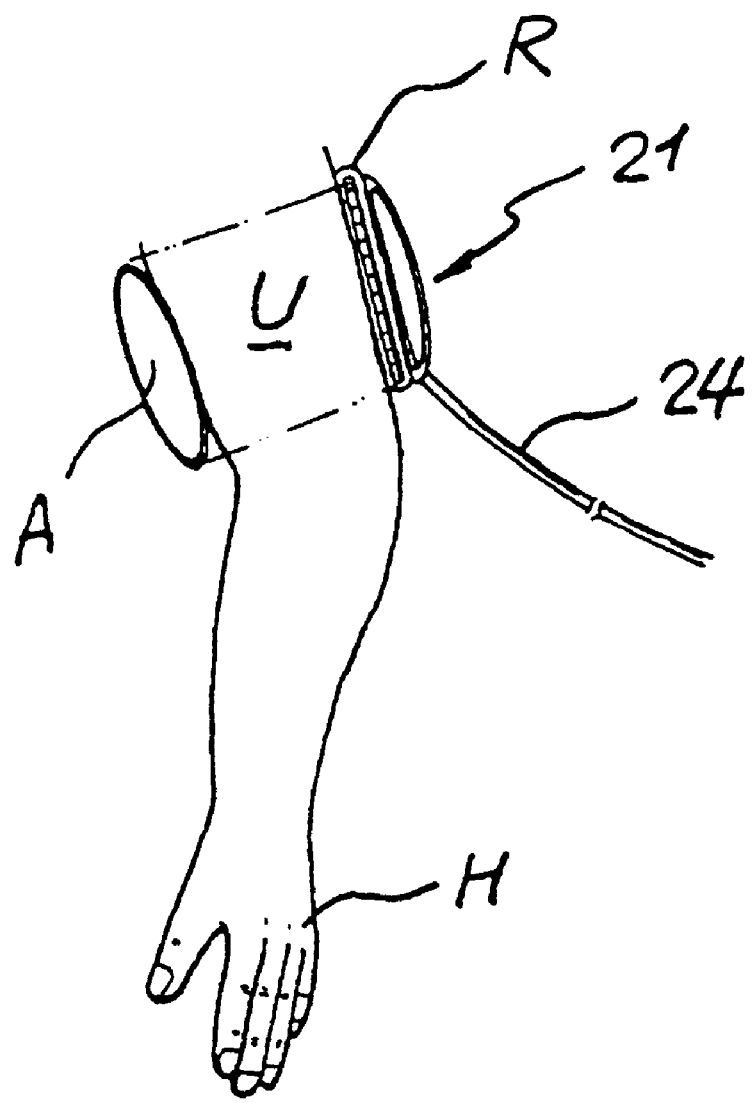

When comparing the blood pressure cuff 1 of the present invention with the conventional blood pressure cuff 21 as shown in FIG. 2, since the blood pressure cuff 1 of the present invention does not have any components made of metal, such as a D-ring or the like, manufacturing cost is lowered due to the fact that the blood pressure cuff 1 is manufactured in a simple manner. Also, pain or stress is not caused to the user when the user independently measures the blood pressure by himself. Furthermore, because possibility for the D-ring to be deformed or detached from the blood pressure cuff 1 is eliminated in advance, semi-permanent use of the blood pressure cuff 1 is ensured.

Consequently, a blood pressure cuff for an independent-measurement type sphygmomanometer which is inexpensive, convenient in use and reliable in operation is provided according to the present invention.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A blood pressure cuff for a sphygmomanometer, adapted for attachment to the upper arm of a user to effect blood pressure measurement for the user, the blood pressure cuff comprising:

an air bag disposed in the blood pressure cuff, said cuff having opposite ends coupled with each other to define a closed loop;

an attachment tab extending from a side of the blood pressure cuff;

a hook and loop fastener strip secured to a surface of the attachment tab; and a complementary hook and loop fastener strip secured to an outer surface of the blood pressure cuff such that it can be engaged with the hook and loop fastener strip, wherein the attachment tab is formed at one end of the blood pressure cuff and the other end of the blood pressure cuff is coupled to a portion of the blood pressure cuff adjacent to the hook and loop fastener strip secured to the attachment tab, and wherein the blood pressure cuff has a width which is gradually decreased in a direction toward the attachment tab.

2. A blood pressure cuff for a sphygmomanometer, adapted for attachment to the upper arm of a user to effect blood pressure measurement for the user, the blood pressure cuff comprising:

an air bag disposed in the blood pressure cuff said cuff having opposite ends coupled with each other to define a closed loop;

an attachment tab extending from a side of the blood pressure cuff;

a hook and loop fastener strip secured to a surface of the attachment tab; and a complementary hook and loop fastener strip secured to an outer surface of the blood pressure cuff such that it can be engaged with the hook and loop fastener strip ends, wherein the blood pressure cuff has a width which is gradually decreased in a direction toward the attachment tab.

* * * * *